United States Patent
Shuey et al.

(10) Patent No.: US 8,063,230 B1
(45) Date of Patent: Nov. 22, 2011

(54) TRIS(N-ARYL BENZIMIDAZOLE)BENZENES AND THEIR USE IN ELECTRONIC DEVICES

(75) Inventors: Steven W. Shuey, Landenberg, PA (US); William J. Delaney, Bear, DE (US); Eric M. Smith, Hockessin, DE (US); Ying Wang, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 545 days.

(21) Appl. No.: 11/305,488

(22) Filed: Dec. 15, 2005

Related U.S. Application Data

(60) Provisional application No. 60/694,920, filed on Jun. 28, 2005, provisional application No. 60/639,057, filed on Dec. 22, 2004.

(51) Int. Cl.
C07D 403/14 (2006.01)
H01J 1/62 (2006.01)
H01J 40/16 (2006.01)

(52) U.S. Cl. ............... 548/310.7; 428/690; 257/40
(58) Field of Classification Search ............... 548/310.7
See application file for complete search history.

(56) References Cited

U.S. PATENT DOCUMENTS

| | | | |
|---|---|---|---|
| 5,645,948 A | 7/1997 | Shi et al. | 428/690 |
| 5,766,779 A * | 6/1998 | Shi et al. | 428/690 |
| 6,171,715 B1 | 1/2001 | Sato et al. | 428/690 |
| 6,303,238 B1 | 10/2001 | Thompson et al. | 428/690 |
| 6,436,558 B1 | 8/2002 | Sato et al. | 428/690 |
| 6,461,747 B1 | 10/2002 | Okada et al. | 428/690 |
| 2001/0019782 A1 | 9/2001 | Igarashi et al. | 428/690 |
| 2002/0037427 A1 * | 3/2002 | Taguchi | 428/690 |

FOREIGN PATENT DOCUMENTS

| | | |
|---|---|---|
| EP | 1 191 612 A2 | 3/2002 |
| EP | 1 191 614 A2 | 3/2002 |
| EP | 1202608 A2 * | 5/2002 |
| JP | 2001-97962 A * | 4/2001 |
| WO | WO 00/70655 | 11/2000 |
| WO | WO 01/41512 A1 | 6/2001 |
| WO | WO 02/02714 A2 | 1/2002 |
| WO | WO 02/15645 A1 | 2/2002 |

OTHER PUBLICATIONS

CA Registry No. 776332-96-8, indexed in the Registry file on STN on Nov. 8, 2004.*
An English translation of JP 2001-097962, 2001.*
O'Brien, D.F., et al., "Electrophosphoresence from a Doped Polymer Light Emitting Diode", *Synthetic Metals*, 2001, 116, (1-3), 379-383.
Campbell, I.H. et al., "Excitation Transfer Processes in a Phosphor-Doped Poly (p-phenylene vinylene) Light-Emitting Diode", *Physical Review. B.*, vol. 65, 085210-1-085210-8, 2002.
Gustafsson, G. et al., Flexible Light-Emitting Diodes made from Soluble Conducting Polymer, *Nature*, 1992, 357, 477-479.
Othmer, K., *Encyclopedia of Chemical Technology*, 1996, 4th edition, 18, 837-860.
Forrest, S.R., "The Path to Ubiquitous and Low-Cost Organic Electronic Appliances on Plastic", *Nature*, 2004, 428, 911-918.

* cited by examiner

*Primary Examiner* — Laura L. Stockton
(74) *Attorney, Agent, or Firm* — Woodcock Washburn LLP

(57) ABSTRACT

The present invention relates to tris(N-aryl-benzimidazole) benzene compounds of the formula:

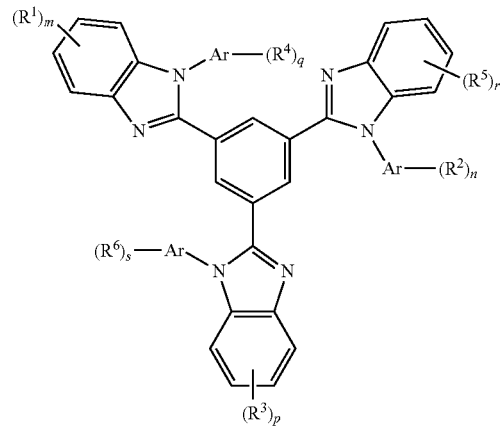

where $R^1$-$R^6$, Ar, m, n, p, q, r, and s are defined in the specification. Also provided are compositions comprising tris (N-aryl-benzimidazole)benzene compounds. The invention also relates to use of such compounds in electronic devices.

17 Claims, 1 Drawing Sheet

TRIS(N-ARYL BENZIMIDAZOLE)BENZENES AND THEIR USE IN ELECTRONIC DEVICES

CROSS-REFERENCE TO RELATED APPLICATIONS

The present application claims benefit to U.S. Provisional Application Ser. Nos. 60/639,057, filed Dec. 22, 2004 and 60/694,920, filed Jun. 28, 2005, each of which are incorporated herein by reference in their entireties.

FIELD OF THE DISCLOSURE

This disclosure relates generally to tris(N-aryl-benzimidazole)benzenes, for example, their use in organic electronic devices, and materials and methods for fabrication of the same.

BACKGROUND INFORMATION

Organic electronic devices convert electrical energy into radiation, detect signals through electronic processes, convert radiation into electrical energy, or include one or more organic semiconductor layers. Most organic electronic devices include a conductive layer (such as a light-emitting or photoactive layer) positioned between two electrodes. In some devices, a charge transport layer can be utilized between the conductive layer and an electrode. For example, a hole transport layer can be positioned between the conductive layer and the anode and a electron transport layer can be positioned between the conductive layer and the cathode.

Thus, what is needed are new materials for use in organic electronic devices.

SUMMARY

In one embodiment, tris(N-aryl-benzimidazole)benzenes compounds having the following formula:

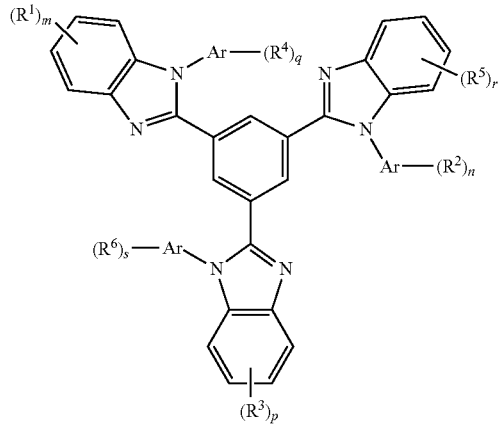

where:

$R^1$, $R^2$, $R^3$, $R^4$, $R^5$, and $R^6$ are each independently H, $C_1$-$C_{20}$ alkyl, halo, $C_1$-$C_{20}$ fluoroalkyl, $C_6$-$C_{20}$ aryl, $C_4$-$C_{20}$ heteroaryl, $C_1$-$C_{20}$ alkoxy, $C_6$-$C_{20}$ aryloxy, $C_1$-$C_{20}$ thioalkoxy, $C_6$-$C_{20}$ thioaryloxy, amino, carboxyl, cyano, nitro, or two adjacent R groups together can be —O—$(CH_2)_t$—O— or a fused aromatic ring;

Ar is $C_6$-$C_{20}$ aryl or $C_4$-$C_{20}$ heteroaryl;

m, n, p, q, r, and s are each independently 0 or an integer from 1 to 3; and t is an integer from 1 to 6, are provided, and methods for making the same, as well as devices and sub-assemblies including the same.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
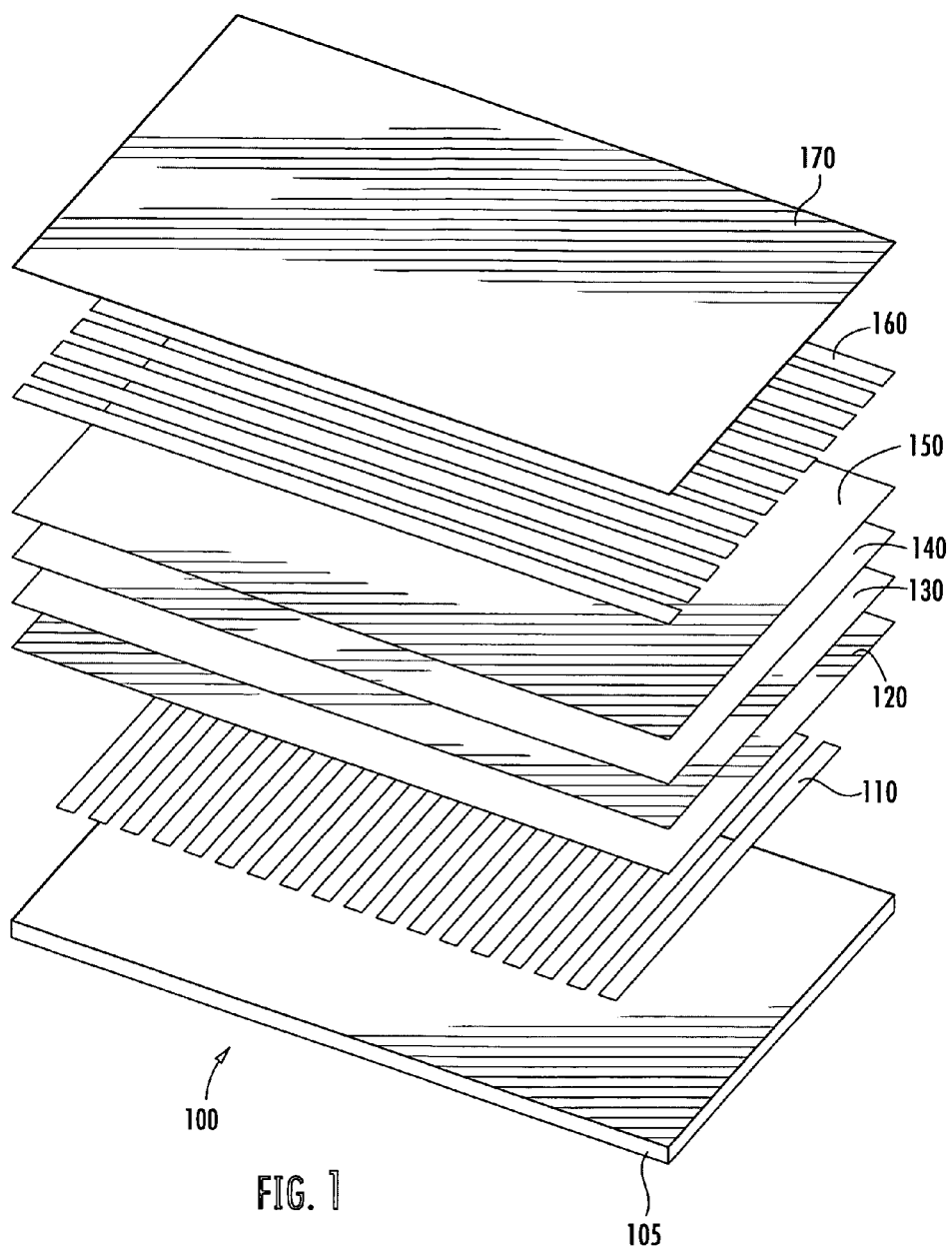
FIG. 1 includes an illustrative example of an organic electronic device that may comprise at least one active layer comprising a tris(N-aryl-benzimidazole)benzenes compound.

The figures are provided by way of example and are not intended to limit the invention. Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

In one embodiment, tris(N-aryl-benzimidazole)benzenes compounds having the following formula:

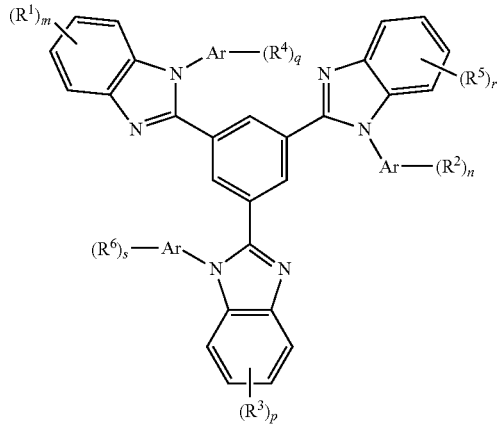

where:

$R^1$, $R^2$, $R^3$, $R^4$, $R^5$, and $R^6$ are each independently H, $C_1$-$C_{20}$ alkyl, halo, $C_1$-$C_{20}$ fluoroalkyl, $C_6$-$C_{20}$ aryl, $C_4$-$C_{20}$ heteroaryl, $C_1$-$C_{20}$ alkoxy, $C_6$-$C_{20}$ aryloxy, $C_1$-$C_{20}$ thioalkoxy, $C_6$-$C_{20}$ thioaryloxy, amino, carboxyl, cyano, nitro, or two adjacent R groups together can be —O—$(CH_2)_t$—O— or a fused aromatic ring;

Ar is $C_6$-$C_{20}$ aryl or $C_4$-$C_{20}$ heteroaryl;

m, n, p, q, r, and s are each independently 0 or an integer from 1 to 3; and t is an integer from 1 to 6;

provided that when Ar is phenyl, at least one of $R^1$-$R^6$ is $C_1$-$C_{20}$ alkyl, halo, $C_1$-$C_{20}$ fluoroalkyl, $C_6$-$C_{20}$ aryl, $C_4$-$C_{20}$ heteroaryl, or two adjacent R groups together can be —O—$(CH_2)_t$—O— are provided.

In one embodiment, when Ar is phenyl, at least one of $R^2$, $R^4$ and $R^6$ is $C_1$-$C_{20}$ alkyl, halo, $C_1$-$C_{20}$ fluoroalkyl, $C_6$-$C_{20}$ aryl, $C_4$-$C_{20}$ heteroaryl, or two adjacent R groups together can be —O—$(CH_2)_t$—O—. In one embodiment, when Ar is phenyl, at least one of $R^1$, $R^3$ and $R^5$ is $C_1$-$C_{20}$ alkyl, halo, $C_1$-$C_{20}$ fluoroalkyl, $C_6$-$C_{20}$ aryl, $C_4$-$C_{20}$ heteroaryl, or two adjacent R groups together can be —O—$(CH_2)_t$—O—.

In one embodiment, Ar is phenyl, naphthyl, or pyridinyl.

$R^1$-$R^6$, in some compounds, are each, independently, H, F, $CF_3$, phenyl, $C_1$-$C_6$ alkyl, or two adjacent R groups can be —O—$CH_2$—O— or a fused aromatic ring.

In one embodiment, $R^1$, $R^2$ and $R^3$ are H. $R^4$, $R^5$, and $R^6$ can each be H in some compounds In one embodiment, $R^4$, $R^5$ and $R^6$ are each independently H, $C_1$-$C_6$ alkyl, F, $CF_3$ or phenyl.

In one embodiment, tris(N-aryl-benzimidazole)benzene compounds are such that m, n, p, q, r, and s are each independently 0 or 1.

In one embodiment, tris(N-aryl-benzimidazole)benzene compounds are illustrated by, but not limited to, the following compounds.

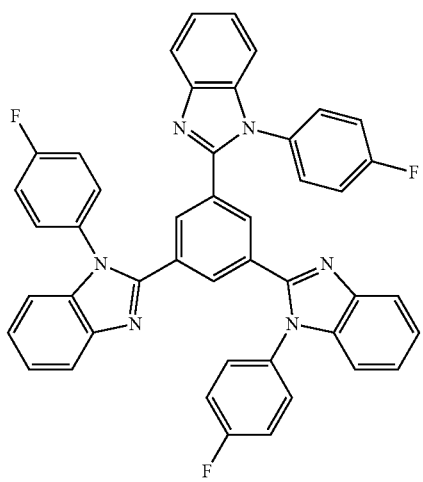

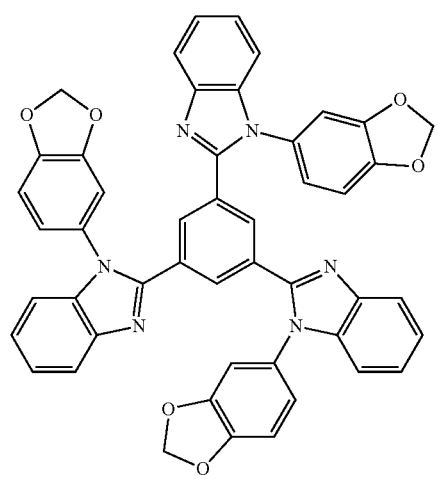

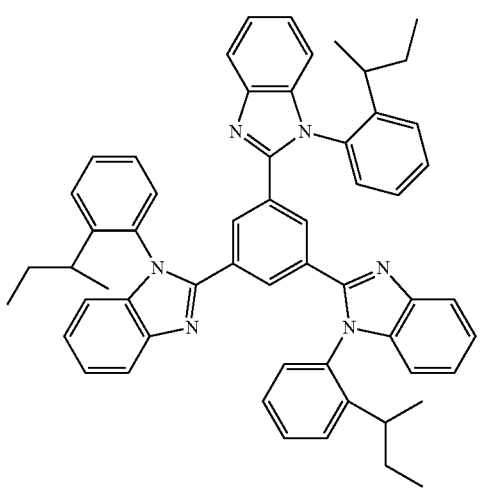

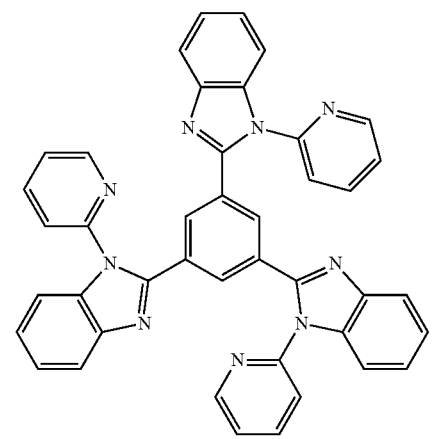

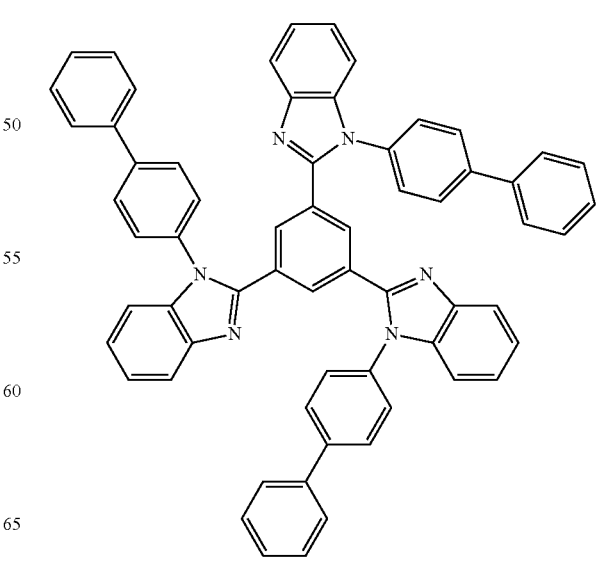

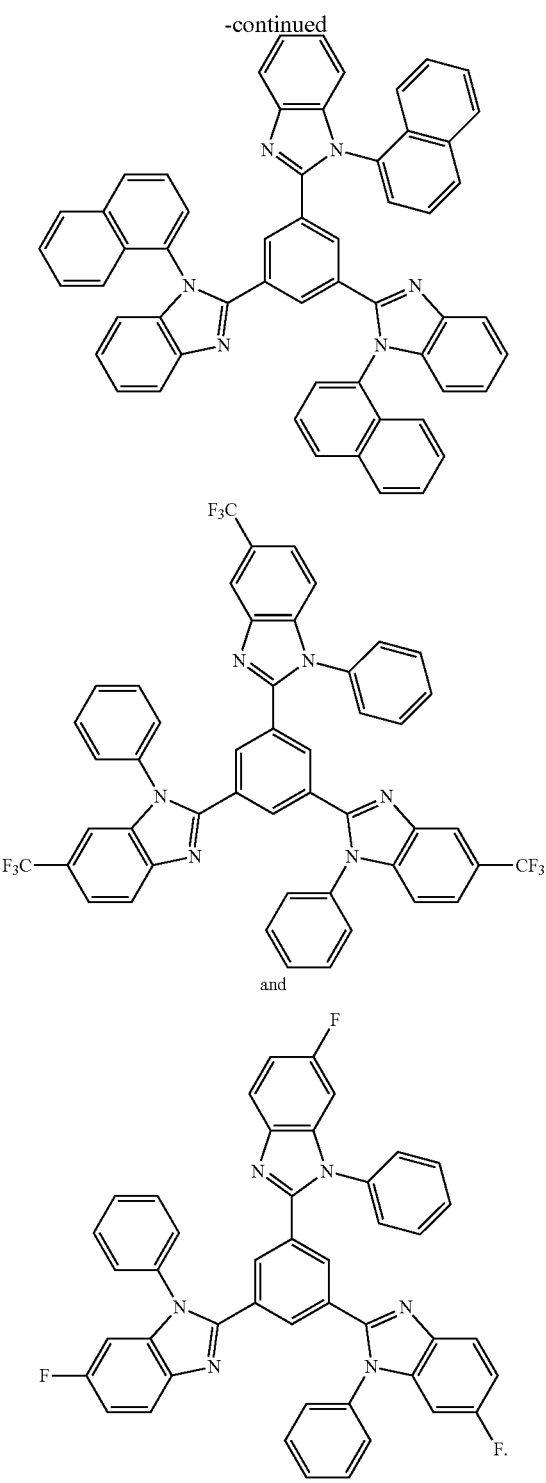

and

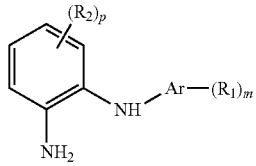

In one embodiment, compositions comprising at least of the above described tris(N-aryl-benzimidazole)benzene compounds can be admixed with a polymer.

In one embodiment, compositions are provided comprising the above-described compounds and at least one solvent, processing aid, charge transporting material, or charge blocking material. These compositions can be in any form, including, but not limited to solvents, emulsions, and colloidal dispersions.

It is to be appreciated that certain features of the invention which are, for clarity, described above and below in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

In one embodiment, the tris(N-aryl-benzimidazole)benzene compounds have charge transport properties.

In one embodiment, the tris(N-aryl-benzimidazole)benzene compounds have a glass transition temperature ("$T_g$") that is higher than the tris(N-aryl-benzimidazole)benzene compounds without $R^1$-$R^6$ substituents. In some cases, the compounds with higher $T_g$ form better films when deposited by either vapor or solution processing methods. In one embodiment, the $T_g$ is greater than 125° C. In another embodiment, the $T_g$ is greater than 130° C.

In one embodiment, provided is an electronic device containing at least one layer having at least one tris(N-aryl-benzimidazole)benzene compound. In one embodiment, the layer is an electron transport layer.

In one embodiment, at least one of the tris(N-aryl-benzimidazole)benzene compounds is included in a charge transport layer, for example, an electron transport layer of an electronic device.

In one embodiment, a composition comprising at least one tris(N-aryl-benzimidazole)benzene compound and at least one of a solvent, a process aid, and a polymer is provided. In one embodiment, the composition comprises a conductive polymer.

In one embodiment, compounds disclosed herein are made by a method comprising the steps of contacting a compound of Formula II:

Formula II $$\text{structure with } (R_2)_p, NH, NH_2, Ar, (R_1)_m$$

with 1,3,5-benzene-tricarbonyl chloride in the presence of a polar aprotic solvent to form an adduct; and subsequently contacting the adduct with a coupling agent to form a compound of Formula I.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Illustrative Electronic Devices, and finally Examples.

1. DEFINITIONS AND CLARIFICATION OF TERMS

Before addressing details of embodiments described below, some terms are defined or clarified.

As used herein, the term "alkyl" includes both branched and straight-chain saturated aliphatic hydrocarbon groups having the specified number of carbon atoms. Unless otherwise indicated, the term is also intended to include cyclic groups. Examples of alkyl groups include methyl, ethyl, propyl, isopropyl, isobutyl, secbutyl, tertbutyl, pentyl, isopentyl cyclopentyl, hexyl, cyclohexyl, isohexyl and the like. The term "alkyl" further includes both substituted and unsubstituted hydrocarbon groups. In some embodiments, the alkyl group may be mono-, di- and tri-substituted. One example of a substituted alkyl group is trifluoromethyl. Other substituted alkyl groups are formed from one or more of the substituents described herein. In certain embodiments alkyl groups have 1 to 12 carbon atoms. In other embodiments, the group has 1 to 6 carbon atoms.

The term "aryl" means an aromatic carbocyclic moiety of up to 20 carbon atoms, which may be a single ring (monocyclic) or multiple rings (bicyclic, up to three rings) fused together or linked covalently. Any suitable ring position of the aryl moiety may be covalently linked to the defined chemical structure. Examples of aryl moieties include, but are not limited to, phenyl, 1-naphthyl, 2-naphthyl, dihydronaphthyl, tetrahydronaphthyl, biphenyl, anthryl, phenanthryl, fluorenyl, indanyl, biphenylenyl, acenaphthenyl, acenaphthylenyl, and the like. In some embodiments, aryl groups have 6 to 20 carbon atoms.

The term "heteroaryl," as used herein, refers to a 5 to 10 membered monocyclic or bicyclic carbon containing aromatic ring having 1 to 3 of its ring members independently selected from nitrogen, sulfur or oxygen. In some embodiments, monocyclic rings have 5 to 6 members. In certain embodiments, bicyclic rings have 8 to 10 membered ring structures. The heteroaryl group may be unsubstituted or substituted. Examples of heteroaryls include, but are not limited to, thienyl, furyl, pyrrolyl, imidazolyl, pyrazolyl, oxazolyl, isoxazolyl, thiazolyl, isothiazolyl, pyridyl, pyrazinyl, pyrimidinyl, pyridazinyl, indolyl, indazolyl, benzofuranyl, isobenzofuranyl, benzothienyl, isobenzothienyl, quinolyl, isoquinolyl, quinoxalinyl, and quinazolinyl.

The term "aryl-alkyl-aryl" refers to a group —Ar"—R"—Ar"— where Ar" is aryl and R" is alkyl as described herein.

The prefix "fluoro" indicates that one or more hydrogen atoms has been replaced with a fluorine atom.

The prefix "thio" indicates that one or more oxygen atoms has been replaced with a sulfur atom.

The term "halogen" includes fluorine, chlorine, iodine, and bromine.

The term "alkoxy," as used herein, refers to the group R—O— where R is an alkyl. In some embodiments, the alkyl has 1 to 4 carbon atoms.

The term "aryloxy," as used herein, refers to the group Ar—O—, where Ar is an aryl group.

As used herein, the term "heteroaryloxy" refers to a group —O—$Ar^H$ where $Ar^H$ is a heteroaryl group as defined herein.

The term "alkenyl" refers to an unsaturated or partially unsaturated aliphatic hydrocarbon group having the specified number of carbon atoms, for example ethenyl, 1-propenyl, 2-butenyl, etc. The term "alkenyl" further includes both unsubstituted and mono-, di- and tri-substituted hydrocarbon groups. Some alkenyl groups have 2 to 7 carbon atoms.

The term "cycloalkyl" includes cyclized alkyl chains having the specified number of carbon atoms, e.g., cyclopropyl, cyclobutyl, cyclopentyl, and cyclohexyl. In some embodiments, cycloalkyl groups have 3 to 8 carbon atoms.

The term "arylalkyl" means aryl-alkyl- wherein the aryl portion, as herein before defined, is suitably substituted on any open ring position with an alkyl moiety wherein the alkyl chain is either a ($C_1$-$C_6$) straight or ($C_3$-$C_7$) branched-chain saturated hydrocarbon moiety. Examples of arylalkyl moieties include, but are not limited to, chemical groups such as benzyl, 1-phenylethyl, 2-phenylethyl, diphenylmethyl, 3-phenylpropyl, 2-phenylpropyl, fluorenylmethyl, and homologs, isomers, and the like.

The term "alkoxycarbonyl" refers to a —$CO_2R^9$ group where $R^9$ is alkyl or aryl.

Unless otherwise indicated, all groups can be substituted or unsubstituted.

An optionally substituted group, such as, but not limited to, alkyl, aryl, or heteroalkyl, may be substituted with one or more substituents which may be the same or different. Suitable substituents include alkyl, aryl, nitro, cyano, —$N(R^7)(R^8)$, halo, hydroxy, carboxy, alkenyl, alkynyl, cycloalkyl, heteroaryl, alkoxy, aryloxy, heteroaryloxy, alkoxycarbonyl, perfluoroalkyl, perfluoroalkoxy, arylalkyl, thioalkoxy, —$S(O)_2$—$N(R^7)(R^8)$, —C(=O)—$N(R^7)(R^8)$, $(R^7)(R^8)$N-alkyl, $(R^7)(R^8)$N-alkoxyalkyl, $(R^7)(R^8)$N-alkylaryloxyalkyl, —$S(O)_s$-aryl (where s=0-2) or —$S(O)_s$-heteroaryl (where s=0-2). Each $R^7$ and $R^8$ is independently an optionally substituted alkyl, cylcoalkyl, or aryl group. $R^7$ and $R^8$, together with the nitrogen atom to which they are bound, can form a ring system in certain embodiments.

The prefix "hetero" indicates that one or more carbon atoms has been replaced with a different atom.

The term "group" is intended to mean a part of a compound, such as a substituent in an organic compound.

The term "organic electronic device" is intended to mean a device including one or more semiconductor layers or materials. Organic electronic devices include, but are not limited to: (1) devices that convert electrical energy into radiation (e.g., a light-emitting diode, light emitting diode display, diode laser, or lighting panel), (2) devices that detect signals through electronic processes (e.g., photodetectors photoconductive cells, photoresistors, photoswitches, phototransistors, phototubes, infrared ("IR") detectors, or biosensors), (3) devices that convert radiation into electrical energy (e.g., a photovoltaic device or solar cell), and (4) devices that include one or more electronic components that include one or more organic semiconductor layers (e.g., a transistor or diode). The term device also includes coating materials for memory storage devices, antistatic films, biosensors, electrochromic devices, solid electrolyte capacitors, energy storage devices such as a rechargeable battery, and electromagnetic shielding applications.

The term "substrate" is intended to mean a workpiece that can be either rigid or flexible and may include one or more layers of one or more materials, which can include, but are not limited to, glass, polymer, metal, or ceramic materials, or combinations thereof.

The term "layer" is used interchangeably with the term "film" and refers to a coating covering a desired area. The area can be as large as an entire device or a specific functional area such as the actual visual display, or as small as a single sub-pixel. Films can be formed by any conventional deposition technique, including vapor deposition and liquid deposition. Liquid deposition techniques include, but are not limited to, continuous deposition techniques such as spin coating, gravure coating, curtain coating, dip coating, slot-die coating, spray-coating, and continuous nozzle coating; and discontinuous deposition techniques such as ink jet printing, gravure printing, and screen printing.

The term "monomer" refers to a compound capable of being polymerized. The term "monomeric unit" refers to units which are repeated in a polymer.

The term "polymeric" is intended to encompass oligomeric species and include materials having 2 or more monomeric units.

The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms which are joined by a bond).

The term "active" when referring to a layer or material is intended to mean a layer or material that exhibits electronic or electro-radiative properties. An active layer material may emit radiation or exhibit a change in concentration of electron-hole pairs when receiving radiation. Thus, the term "active material" refers to a material which electronically facilitates the operation of the device. Examples of active materials include, but are not limited to, materials which conduct, inject, transport, or block a charge, where the charge can be either an electron or a hole. Examples of inactive materials include, but are not limited to, planarization materials, insulating materials, and environmental barrier materials.

As used herein, the term "photoactive" refers to a material that emits light when activated by an applied voltage (such as in a light-emitting diode or light-emitting electrochemical cell), or responds to radiant energy and generates a signal with or without an applied bias voltage (such as in a photodetector): An example of a photoactive layer is an emitter layer.

As used herein, the term "charge transport," when referring to a layer or material is intended to mean such layer or material facilitates migration of such charge through the thickness of such layer, material, member, or structure with relative efficiency and small loss of charge, and is meant to be broad enough to include materials that may act as a hole transport or an electron transport material. The term "electron transport" when referring to a layer or material means such a layer or material, member or structure that promotes or facilitates migration of electrons through such a layer or material into another layer, material, member or structure.

The term "charge blocking," when referring to a layer, material, member, or structure, is intended to mean such layer, material, member or structure reduces the likelihood that a charge migrates into another layer, material, member or structure. The term "electron blocking" when referring to a layer, material, member or structure is intended to mean such layer, material, member or structure that reduces that likelihood that electrons migrate into another layer, material, member or structure.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The use of "a" or "an" are employed to describe elements and components of the invention. This is done merely for convenience and to give a general sense of the invention. This description should be read to include one or at least one and the singular also includes the plural unless it is obvious that it is meant otherwise.

Group numbers corresponding to columns within the Periodic Table of the elements use the "New Notation" convention as seen in the CRC Handbook of Chemistry and Physics, 81st Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

2. ILLUSTRATIVE ELECTRONIC DEVICES

Referring to FIG. 1, an exemplary organic electronic device 100 is shown. The device 100 includes a substrate 105. The substrate 105 may be rigid or flexible, for example, glass, ceramic, metal, or plastic. When voltage is applied, emitted light is visible through the substrate 105.

A first electrical contact layer 110 is deposited on the substrate 105. For illustrative purposes, the layer 110 is an anode layer. Anode layers may be deposited as lines. The anode can be made of, for example, materials containing or comprising metal, mixed metals, alloy, metal oxides or mixed-metal oxide. The anode may comprise a conducting polymer, polymer blend or polymer mixtures. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode may also comprise an organic material, especially a conducting polymer such as polyaniline, including exemplary materials as described in Flexible Light-Emitting Diodes Made From Soluble Conducting Polymer, Nature 1992, 357, 477-479. At least one of the anode and cathode should be at least partially transparent to allow the generated light to be observed.

An optional buffer layer 120, such as hole transport materials, may be deposited over the anode layer 110, the latter being sometimes referred to as the "hole-injecting contact layer." Examples of hole transport materials suitable for use as the layer 120 have been summarized, for example, in Kirk Othmer, Encyclopedia of Chemical Technology, Vol. 18, 837-860 (4th ed. 1996). Both hole transporting "small" molecules as well as oligomers and polymers may be used. Hole transporting molecules include, but are not limited to: N,N' diphenyl-N,N'-bis(3-methylphenyl)-[1,1'-biphenyl]-4,4'-diamine (TPD), 1,1 bis[(di-4-tolylamino)phenyl]cyclohexane (TAPC), N,N' bis(4-methylphenyl)-N,N'-bis(4-ethylphenyl)-[1,1'-(3,3'-dimethyl)biphenyl]-4,4'-diamine (ETPD), tetrakis (3-methylphenyl)-N,N,N',N'-2,5-phenylenediamine (PDA), a-phenyl 4-N,N-diphenylaminostyrene (TPS), p (diethylamino)benzaldehyde diphenylhydrazone (DEH), triphenylamine (TPA), bis[4 (N,N-diethylamino)-2-methylphenyl](4-methylphenyl)methane (MPMP), 1 phenyl-3-[p-(diethylamino) styryl]-5-[p-(diethylamino)phen yl]pyrazoline (PPR or DEASP), 1,2 trans-bis(9H-carbazol-9-yl)cyclobutane (DCZB), N,N,N',N' tetrakis(4-methylphenyl)-(1,1'-biphenyl)-4,4'-diamine (TTB), and porphyrinic compounds, such as copper phthalocyanine. Useful hole transporting polymers include, but are not limited to, polyvinylcarbazole, (phenylmethyl)polysilane, and polyaniline. Conducting polymers are useful as a class. It is also possible to obtain hole transporting polymers by doping hole transporting moieties, such as those mentioned above, into polymers such as polystyrenes and polycarbonates.

An organic layer 130 may be deposited over the buffer layer 120 when present, or over the first electrical contact layer 110. In some embodiments, the organic layer 130 may be a number of discrete layers comprising a variety of components. Depending upon the application of the device, the organic layer 130 can be a light-emitting layer that is activated by an applied voltage (such as in a light-emitting diode or light-emitting electrochemical cell), or a layer of material that responds to radiant energy and generates a signal with or without an applied bias voltage (such as in a photodetector).

Other layers in the device can be made of any materials which are known to be useful in such layers upon consideration of the function to be served by such layers.

Any organic electroluminescent ("EL") material can be used as a photoactive material (e.g., in layer 130). Such materials include, but are not limited to, fluorescent dyes, small molecule organic fluorescent compounds, fluorescent and phosphorescent metal complexes, conjugated polymers, and mixtures thereof. Examples of fluorescent dyes include, but are not limited to, pyrene, perylene, rubrene, derivatives thereof, and mixtures thereof. Examples of metal complexes include, but are not limited to, metal chelated oxinoid compounds, such as tris(8-hydroxyquinolato)aluminum ($Alq_3$); cyclometalated iridium and platinum electroluminescent compounds, such as complexes of Iridium with phenylpyridine, phenylquinoline, or phenylpyrimidine ligands as disclosed in Petrov et al., Published PCT Application WO 02/02714, and organometallic complexes described in, for example, published applications US 2001/0019782, EP 1191612, WO 02/15645, and EP 1191614; and mixtures thereof. Electroluminescent emissive layers comprising a charge carrying host material and a metal complex have been described by Thompson et al., in U.S. Pat. No. 6,303,238, and by Burrows and Thompson in published PCT applications WO 00/70655 and WO 01/41512. Examples of conjugated polymers include, but are not limited to poly(phenylenevinylenes), polyfluorenes, poly(spirobifluorenes), polythiophenes, poly(p-phenylenes), copolymers thereof, and mixtures thereof.

In one embodiment of the devices of the invention, photoactive material can be an organometallic complex. In another embodiment, the photoactive material is a cyclometalated complex of iridium or platinum. Other useful photoactive materials may be employed as well. Complexes of iridium with phenylpyridine, phenylquinoline, or phenylpyrimidine ligands have been disclosed as electroluminescent compounds in Petrov et al., Published PCT Application WO 02/02714. Other organometallic complexes have been described in, for example, published applications US 2001/0019782, EP 1191612, WO 02/15645, and EP 1191614. Electroluminescent devices with an active layer of polyvinyl carbazole (PVK) doped with metallic complexes of iridium have been described by Burrows and Thompson in published PCT applications WO 00/70655 and WO 01/41512. Electroluminescent emissive layers comprising a charge carrying host material and a phosphorescent platinum complex have been described by Thompson et al., in U.S. Pat. No. 6,303,238, Bradley et al., in Synth. Met. 2001, 116 (1-3), 379-383, and Campbell et al., in Phys. Rev. B, Vol. 65 085210.

A second electrical contact layer 160 is deposited on the organic layer 130. For illustrative purposes, the layer 160 is a cathode layer.

Cathode layers may be deposited as lines or as a film. The cathode can be any metal or nonmetal having a lower work function than the anode. Exemplary materials for the cathode can include alkali metals, especially lithium, the Group 2 (alkaline earth) metals, the Group 12 metals, including the rare earth elements and lanthanides, and the actinides. Materials such as aluminum, indium, calcium, barium, samarium and magnesium, as well as combinations, can be used. Lithium-containing and other compounds, such as LiF and $Li_2O$, may also be deposited between an organic layer and the cathode layer to lower the operating voltage of the system.

An electron transport layer 140 or electron injection layer 150 is optionally disposed adjacent to the cathode, the cathode being sometimes referred to as the "electron-injecting contact layer."

An encapsulation layer 170 is deposited over the contact layer 160 to prevent entry of undesirable components, such as water and oxygen, into the device 100. Such components can have a deleterious effect on the organic layer 130. In one embodiment, the encapsulation layer 170 is a barrier layer or film.

Though not depicted, it is understood that the device 100 may comprise additional layers. For example, there can be a layer (not shown) between the anode 110 and hole transport layer 120 to facilitate positive charge transport and/or bandgap matching of the layers, or to function as a protective layer. Other layers that are known in the art or otherwise may be used. In addition, any of the above-described layers may comprise two or more sub-layers or may form a laminar structure. Alternatively, some or all of anode layer 110 the hole transport layer 120, the electron transport layers 140 and 150, cathode layer 160, and other layers may be treated, especially surface treated, to increase charge carrier transport efficiency or other physical properties of the devices. The choice of materials for each of the component layers is preferably determined by balancing the goals of providing a device with high device efficiency with device operational lifetime considerations, fabrication time and complexity factors and other considerations appreciated by persons skilled in the art. It will be appreciated that determining optimal components, component configurations, and compositional identities would be routine to those of ordinary skill of in the art.

In one embodiment, the different layers have the following range of thicknesses: anode 110, 500-5000 Å, in one embodiment 1000-2000 Å; hole transport layer 120, 50-2000 Å, in one embodiment 200-1000 Å; photoactive layer 130, 10-2000 Å, in one embodiment 100-1000 Å; layers 140 and 150, 50-2000 Å, in one embodiment 100-1000 Å; cathode 160, 200-10000 Å, in one embodiment 300-5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

In operation, a voltage from an appropriate power supply (not depicted) is applied to the device 100. Current therefore passes across the layers of the device 100. Electrons enter the organic polymer layer, releasing photons. In some OLEDs, called active matrix OLED displays, individual deposits of photoactive organic films may be independently excited by the passage of current, leading to individual pixels of light emission. In some OLEDs, called passive matrix OLED displays, deposits of photoactive organic films may be excited by rows and columns of electrical contact layers.

Devices can be prepared employing a variety of techniques. These include, by way of non-limiting exemplification, vapor deposition techniques and liquid deposition. Devices may also be sub-assembled into separate articles of manufacture that can then be combined to form the device.

3. EXAMPLES

The concepts described herein will be further described in the following examples, which do not limit the scope of the invention described in the claims.

All percentages are by weight, unless otherwise indicated.

Example 1

1,3,5-Tris-(2-[1-(4-fluorophenyl)-1H-benzimidazoyl])benzene

To a 100 mL round bottom flask was added 17.25 g of 4-fluoroaniline (Aldrich) and 10.95 g of 1-fluoro-2-nitrobenzene (Aldrich). The mixture was stirred under $N_2$ atmosphere while 4.5 g of anhydrous KF was added. The flask was fitted with a condenser and heated to 180° C. under $N_2$ for 48 h. The reaction mixture was cooled to 25° C. and diluted with 200 mL of methylene chloride. Extraction with 2×200 mL of water, 4×200 mL of 1M HCl, and 2×200 mL of water, followed by drying over $MgSO_4$ and removal of solvent gave a brown oil. Purification on silica gel eluting with 50% $CH_2Cl_2$ in hexanes gave 17.13 g of an orange solid, 4-fluorophenyl-(2-nitrophenyl)-amine.

The orange solid (17.0 g) was dissolved in 350 mL of MeOH and added to a 1-liter flask. To this mixture was added 19.57 g of $NH_4Cl$ and 71.8 g of Zn dust. The mixture was vigorously stirred under an $N_2$ atmosphere while heating to 55° C. for 1 h. The mixture was cooled and filtered and the residue washed with MeOH. The combined filtrates were concentrated in vacuo to give a red oil which was re-dissolved in EtOAc and washed with water. The organic layer was dried over $MgSO_4$ and concentrated to give a red oil which was dissolved in $CH_2Cl_2$ and filtered through silica gel. After removal of the solvent a light pink solid 4-fluorophenyl-(2-aminophenyl)amine, 12.6 g, was obtained.

To a 50 mL flask was added 2.0 g of the above material along with 20 mL of NMP. In a separate flask, 0.875 g of 1,3,5-benzenetricarbonyl trichloride was dissolved in 10 mL of NMP and added in portions to the first solution under an $N_2$ atmosphere. After addition the mixture was allowed to stir at 25° C. for 30 min. The mixture was poured into 100 mL of 5% $NaHCO_3$ with vigorous mixing. The resulting precipitate was filtered off and washed repeatedly with water, then dried in vacuo overnight. The solid was suspended in MeOH and filtered to give a white solid which was dried to yield 4.46 g of the triamide material. The white solid, 0.5 g, was weighed into a flask under an $N_2$ atmosphere and heated to 225° C. until no more water was evolved. The flask was cooled and the contents purified by preparative TLC to give the desired tris (N-aryl-benzimidazole)benzene. The Tg of the material was 127° C.

Example 2

1,3,5-Tris-(2-[1-phenyl)-5-trifluoromethyl-1H-benzimidazoyl])benzene

To a 100 mL flask equipped with a magnetic stir bar was added 2.23 g of aniline and 3.75 mL of 4-fluoro-3-nitrobenzotrifluoride. To the resulting mixture was added 1.38 g of KF and the mixture was heated at 100° C. with stirring for 48 h. After cooling to 25° C., the reaction mixture was extracted 3× with 50 mL of methylene chloride and the combined extracts washed 3×200 mL water and once with 150 mL of brine. Drying of the organics over $Na_2SO_4$ followed by evaporation of the solvent left 5.85 g of a yellow solid which was suitable for the next step.

Into a 500 mL flask was added 4.0 g of the yellow solid from the above step 3.85 g of $NH_4Cl$ and 150 mL of MeOH. The solution was cooled in an ice/water bath with vigorous stirring while 13.9 g of Zinc dust was added. The reaction mixture was stirred for 10 min producing a color change from bright orange to pale green. The Zn was filtered off and washed with MeOH. The combined filtrates were concentrated and the resulting oil purified by filtration through a silica column with 50% $CH_2Cl_2$ in hexanes. The expected diamine compound, 3.35 g, was obtained as a tan solid.

The tan solid (1.0 g) was charged to a 100 mL flask and dissolved in 20 mL of NMP. A solution of 350 mg of 1,3,5-benzene tricarbonyl trichloride in 5 mL of NMP was prepared and added to the 100 mL flask in small portions. After stirring under $N_2$ for 1 h, the mixture was poured into 125 mL of 5% $NaHCO_3$ with stirring. The resulting white precipitate was filtered off, washed with water and hexanes and dried in vacuo to give 1.65 g of a white solid which proved to be the desired triamide.

The triamide, 400 mg, was weighed into a flask and heated to 200° C. under $N_2$ for 4 h. The resulting material was purified by prep TLC developing with 2% MeOH/methylene chloride to give 184 mg of the desired tris-benzimidazole. The Tg of the material was 123° C.

Example 3

1,3,5-Tris-(2-[1-(3,4-methylenedioxyphenyl)-1H-benzimidazoyl])benzene

To a 100 mL flask equipped with a stir bar and condenser, was added 7.6 g of 3,4-methylenedioxyaniline, 7.82 g of 2-fluoronitrobenzene and 3.2 g of KF. The mixture was heated to 160° C. in an oil bath for 48 h, then cooled to 25° C. and extracted into 200 mL of methylene chloride. The extracts were washed 2×200 mL of water, 4×200 mL of 1M $NaHCO_3$, 1×200 mL of brine, then dried over $MgSO_4$. The solvent was removed and the crude material was purified by flash chromatography on silica gel, eluting with 20% methylene chloride/hexanes to give 13.34 g of the desired adduct.

Into a 250 mL flask was added 7.06 g of the product from the previous step, 2.24 g of $NH_4Cl$ and 150 mL of MeOH. The solution was stirred under $N_2$ while 8.2 g of zinc dust was added. The mixture was stirred for 1 h, then filtered and the solids washed with MeOH. The combined filtrates were concentrated to a red oil, which was purified by column chromatography, eluting with methylene chloride to give 5.5 g of the desired diamine.

The diamine, 2.0 g, was weighed into a 50 mL flask and dissolved in 20 mL of NMP. A solution of 1,3,5 benzene tricarbonyl trichloride, 0.775 g, in 10 mL NMP, was then added and the mixture was stirred under $N_2$ for 16 h. The mixture was then poured into 100 mL 5% $NaHCO_3$ and the resulting precipitate collected and washed with water. The solid was suspended in MeOH, filtered, dried, and recrystallized from methylene chloride/MeOH to give 4.76 g.

Into a 20 mL flask was weighed 500 mg of the above solid. The flask and contents were heated to 215° C. in an oil bath for 2 h then cooled to 25° C. The solid reaction mixture was extracted into methylene chloride and purified by preparative TLC, eluting with 5% MeOH/methylene chloride to give 300 mg of the desired tris(N-aryl-benzimidazole)benzene. The Tg of the material was 140° C.

Example 4

1,3,5-Tris-(2-[1-(2-sec-butylphenyl)-1H-benzimidazoyl])benzene

To a 100 mL round bottom (RB) flask with a stir bar was added 26.83 mL of aniline and 9.07 mL of 2-fluoro-nitrobenzene. KF (5.0 g) was added in one portion and the mixture stirred under an $N_2$ atmosphere at 180° C. for 48 h. The mixture was cooled to 25° C. and extracted with 200 mL of methylene chloride. The methylene chloride extracts were then washed with 2×200 mL of water, 4×200 mL of 1M HCl, and 2×200 mL of water. Drying over $MgSO_4$ followed by evaporation of the solvent gave the crude material which was purified by chromatography on silica gel, eluting with 20% methylene chloride/hexanes. The desired product (23.5 g) was obtained.

To a 1-liter flask was added 22.4 g of the above product, 22.16 g of $NH_4Cl$, 81.27 g of Zn dust and 400 mL of MeOH. The mixture was heated to 70° C. for 1 h then cooled to 25° C. The solids were filtered off and washed with MeOH. The combined MeOH fractions were concentrated to give a red oil which was purified on silica gel, eluting with 40% methylene chloride/hexanes to give 17.8 g of a red oil.

To a 50 mL flask was added 2.0 g of the above material along with 20 mL of NMP. To this solution was added a solution of 0.54 g of 1,3,5-benzene tricarbonyl trichloride in 10 mL NMP. The mixture was allowed to stir for 30 min and then poured into 100 mL of 5% $NaHCO_3$. The resulting precipitate was filtered off and washed with water to furnish the triamide suitable for the next step.

Into a 50 mL flask was added 2.0 g of 1-(diphenyl-phosphinoyl)-4-methyl-piperazine and 10 mL of dichloroethane. The mixture was cooled to 0° C. in an ice bath while a solution of 1.0 mL of triglic anhydride in 5 mL of methylene chloride was added. After stirring for 30 min a red oil separated from the reaction mixture. In a separate flask 1.76 g of the triamide solution from the above step was dissolved in 60 mL of dichloroethane in a 250 mL flask. To this mixture was added the contents of the first flask by syringe. A clear solution was formed immediately and the mixture was allowed to stir for an additional 1 h. The mixture was extracted with 5% $HaHCO_3$ 3×100 mL, water, and brine then dried over $MgSO_4$. Evaporation of the solvent followed by silica chromatography eluting with 20% EtOAc/hexanes gave the desired tris (N-aryl-benzimidazole)benzene as a tan solid.

Example 5

1,3,5-Tris-(2-[1-(2pyridyl)-1H-benzimidazoyl])benzene

To a 100 mL flask fitted with a condenser and $N_2$ inlet and a stir bar was added 14.60 g of 2-aminopyridine and 8.18 mL of 2-fluoronitrobenzene. In one portion was added 4.50 g of KF, and the mixture was heated to 180° C. in an oil bath for 48 hrs. The reaction mixture was cooled to room temperature and extracted into 200 mL of methylene chloride then washed with: 2×200 mL of water, 4×200 mL of 1M HCl, 2×200 mL of water. The organic layer was dried with $MgSO_4$ and evaporated to give an oil. The crude oil was purified by silica chromatography, eluting the pure orange product with 75% DCM/hexane to 100% DCM. Combined and concentrated the fractions to an orange powder and dried on high vacuum overnight to give 1.8 g of the desired material suitable for use in the next step.

Into a 500 mL flask was weighed 1.8 g of the intermediate from the above step along with 2.24 g of $NH_4Cl$, 8.2 g of Zn dust and 175 mL of MeOH. The mixture was stirred for 1 h at which time the color of the solution had gone from yellow to nearly colorless. The solids were filtered off and washed with MeOH and the combined organic materials were concentrated and purified by silica chromatography eluting with 5% MeOH/methylene chloride to give 1.7 g of a material suitable for use in the next step.

To a 50 mL flask, 0.5 g of the above material was dissolved in 20 mL of NMP. A solution of 0.24 g of 1,3,5 benzene tricarbonyl trichloride in 10 mL of NMP was added and the mixture stirred for 30 min. The reaction mixture was poured into 100 mL of 5% $NaHCO_3$ and the resulting precipitate was washed repeatedly with water. The resulting solid was suspended in MeOH filtered and the solids (575 mg) which were suitable for use in the next step were dried under vacuum.

To a 50 mL flask was added 250 mg of the above intermediate. The flask was flushed with $N_2$ and heated to 165° C. for 4 h. After cooling The product was extracted into methylene chloride and purified by preparative TLC developing with 10% MeOH/methylene chloride. The Tg of the desired tris (N-aryl-benzimidazole)benzene was 116° C.

Example 6

1,3,5-Tris-(2-[1-(phenyl)-6-fluoro-1H-benzimidazoyl])benzene

To a 100 mL flask equipped with a condenser, an $N_2$ inlet and a stir bar was added 2.93 g of aniline, 3.45 mL of 2,4-difluoronitrobenzene, and 1.82 g of KF. The mixture was heated to 180° C. with stirring for 63 h. After cooling to room temperature, the crude material was extracted into methylene chloride and washed with water and brine. The extracts were dried over $MgSO_4$ and the solvent removed to give the crude product which was purified by silica gel column chromatography eluting with 50% methylene chloride/hexanes to give 4.44 g of yellow powder.

The yellow powder (4.3 g) from the previous step, 5.37 g of $NH_4Cl$, 18.16 g of Zn dust and 150 mL of 2:1 MeOH:toluene were mixed in a 500 mL flask. The mixture was stirred for 10 min and then heated to reflux for 1 h. The solids were filtered off and washed with MeOH. The combined organic materials were concentrated to a brown oil and chromatographed on silica gel eluting with 50% methylene chloride/hexanes to give 3.3 g of off white solid suitable for use in the next step.

The solid from the previous step (3.3 g) was dissolved in 20 mL of NMP and added to a 100 mL flask along with 1.44 g of 1,3,5 benzene tricarbonyl trichloride. The reaction mixture was stirred for 1 h at 25° C. then heated to 55° C. an additional 1 h. After cooling the mixture was poured into 125 mL of 5% $NaHCO_3$ and the resulting precipitate collected by filtration. The precipitate was washed with water and dried to give the desired product suitable for use in the next step, (4.18 g).

The intermediate from the above step 400 mg, was weighed into a 10 mL flask and heated to 200° C. for 4 h under $N_2$. Purification of the crude product was achieved by preparative TLC, developing with 2% MeOH/methylene chloride to give 214 mg of the desired tris(N-aryl-benzimidazole)benzene. The Tg of the material was 125° C.

Example 7

1,3,5-Tris-(2-[1-(1-Naphthyl)-1H-benzimidazoyl])benzene

To a 100 mL one neck flask was added 3.5 g of 1-fluoro-2-nitrobenzene and 3.5 g of 1-amino-naphthalene followed by 7.09 g of KF. The reaction mixture was heated under $N_2$ to 180° C. for 46 h, then cooled and extracted into 250 mL or methylene chloride. The extracts were washed with 150 mL each of water, 5% $NaHCO_3$ and brine before drying over $Na_2SO_4$ and removing the solvent to give 3.5 g of an oil. The oil was purified by flash chromatography on silica gel, eluting with 7:3 hexanes/methylene chloride to give 3.33 g of a yellow solid suitable for use in the next step.

Into a 500 mL flask was added 2.3 g of the above solid along with 120 mL of ethanol and 2.31 g of $NH_4Cl$. To this mixture was added 8.47 g of Zn dust and the resulting suspension was stirred for 40 min followed by heating to 70° C. for 30 min and refluxing for 50 m. An additional 4.2 g of Zn dust was added and the mixture refluxed overnight. The reaction mixture was cooled to room temperature and filtered through celite. The celite pad was washed with ethanol and the combined filtrates were concentrated to a solid (3.1 g). The solid was purified by flash chromatography eluting with 7:3 methylene chloride/hexanes followed by 3% methanol/methylene chloride to give 206 g of material suitable for use in the next step.

Into a 250 mL flask was added 1.89 g of the above material and 30 mL of methylene chloride. To this solution was added a solution of 0.714 g of 1,3,5-benzene tricarbonyl trichloride in 4 mL of methylene chloride. The resulting yellow solution was stirred for 1 h and poured into ice water. The resulting precipitate was filtered and washed with water and hexanes then dried to give 2.5 g of a yellow solid suitable for use in the next step.

Into a 100 mL flask was added 2.5 g of the above material and the flask was heated under $N_2$ for 1.25 h. After cooling to room temperature, the product was purified by flash chromatography on silica gel eluting with 1:1 hexanes/ethyl acetate to give 0.805 g of the d desired tris(N-aryl-benzimidazole)benzene. The Tg of the material was 148° C.

Example 8

1,3,5-Tris-(2-[1-(p-biphenyl)-1H-benzimidazoyl])benzene

To a mixture of 10.15 g of 4-aminobipheny and 8.48 g of 2-nitro-fluorobenzene was added 3.48 g of KF. The resulting mixture was heated to 180° C. for 60 h. After cooling the mass was extracted into methylene chloride and concentrated to a brown solid. Purification by flash chromatography on silica gel eluting with 7:3 hexane/methylene chloride gave the desired product (15.87 g) as an orange solid.

Into a 500 mL flask was weighed 5.0 g of the intermediate from the above step along with 4.6 g of $NH_4Cl$, 16.6 g of Zn dust and 175 mL of MeOH. The mixture was stirred for 1 h. The solids were filtered off and washed with MeOH and the combined organic materials were concentrated and purified by silica chromatography eluting with 4% MeOH/methylene chloride to give 2.9 g of a material suitable for use in the next step.

To a 250 mL flask was added 2.0 g of the above material and 40 mL of methylene chloride. To this solution was added a solution of 0.68 g of 1,3,5-benzenetricarbonyl trichloride in 5 mL of methylene chloride. The solution was stirred for 30 min then heated to reflux an additional 30 min. The reaction mixture was concentrated to about 5 mL and run through a silica gel column, elution with 3% MeOH/methylene chloride to give the desired product 1.44 g suitable for use in the next step.

Into a 100 mL flask was added the above intermediate. The flask was heated to 180° C. for 2 h. After cooling the solid material was chromatographed on silica gel, eluting with 1.5% MeOH/methylene chloride then 3.5% methylene chloride to give 310 mg of the desired tris(N-aryl-benzimidazole)benzene. The Tg of the material was 141° C.

Examples 9-16

OLED Devices

These examples illustrate the use of the compounds of the present invention in an organic electronic device, for example an OLED device.

General Procedure

OLED devices were fabricated by the thermal evaporation technique. The base vacuum for all of the thin film deposition was in the range of $10^{-6}$ torr. The deposition chamber was capable of depositing eight different films without the need to break the vacuum. Patterned indium tin oxide coated glass substrates (ITOs) from Thin Film Devices, Inc were used. These ITOs are based on Corning 1737 glass coated with 1400 Å ITO coating, with sheet resistance of 30 ohms/square and 80% light transmission. The patterned ITO substrates were then cleaned ultrasonically in aqueous detergent solution. The substrates were then rinsed with distilled water, followed by isopropanol, and then degreased in toluene vapor.

The cleaned, patterned ITO substrate was then loaded into the vacuum chamber and the chamber was pumped down to $10^{-6}$ torr. The substrate was then further cleaned using an oxygen plasma for about 5 minutes. After cleaning, multiple layers of thin films were then deposited sequentially onto the substrate by thermal evaporation. Patterned metal electrodes (Al or LiF/Al) were deposited through a mask. The thickness of the films was measured during deposition using a quartz crystal monitor. The completed OLED device was then taken out of the vacuum chamber and characterized immediately without encapsulation.

The OLED samples were characterized by measuring their (1) current-voltage (I-V) curves, (2) electroluminescence radiance versus voltage, and (3) electroluminescence spectra versus voltage. The I-V curves were measured with a Keithley Source-Measurement Unit Model 237. The electroluminescence radiance (in units of $cd/m^2$) vs. voltage was measured with a Minolta LS-110 luminescence meter, while the voltage was scanned using the Keithley SMU. The electroluminescence spectrum was obtained by collecting light using an optical fiber, through an electronic shutter, dispersed through a spectrograph, and then measured with a diode array detector. All three measurements were performed at the same time and controlled by a computer. The efficiency of the device at a certain voltage is determined by dividing the electroluminescence radiance of the LED by the current density needed to run the device. The unit is a cd/A.

The devices had the structure shown in FIG. 1. Layer 140 was either a tris(N-aryl-benzimidazole)benzene compound, or, in the comparative example, the unsubstituted 1,3,5-tris-(2-[1-(phenyl)-1H-benzimidazoyl])benzene ("TPBI"). TPBI can be made as described in U.S. Pat. No. 5,645,948, Examples 1 and 2. TPBI has a Tg of 122.7° C. The materials had the structures shown below.

TPBI:

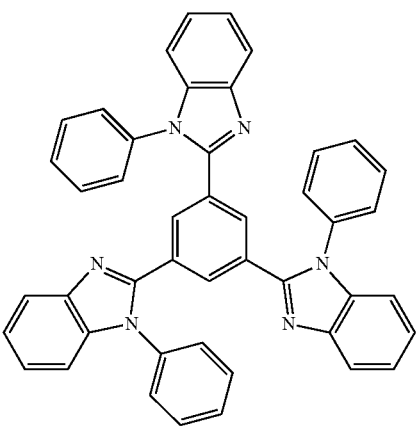

MPMP:

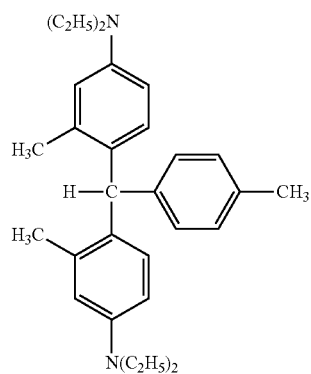

G1, a green emitter:

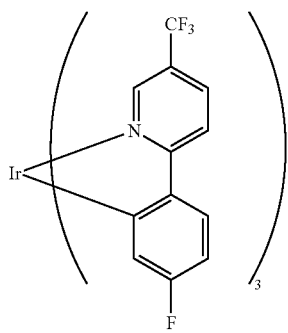

AlQ:

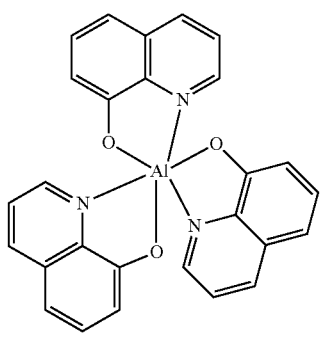

Device materials and layer thicknesses are summarized in Table 1. The device properties are given in Table 2.

TABLE 1

Device Architecture

| Example | Layer 120 | Layer 130 | Layer 140 | Layer 150 | Layer 160 |
|---|---|---|---|---|---|
| Comp. A | MPMP 305 | G1 406 | TPBI 102 | AlQ 304 | LiF - 10 Al - 505 |
| 9 | MPMP 302 | G1 403 | Compound of example 4 102 | AlQ 305 | LiF - 10 Al - 505 |
| 10 | MPMP 301 | G1 403 | Compound of example 1 103 | AlQ 302 | LiF - 10 Al - 503 |
| 11 | MPMP 303 | G1 403 | Compound of example 2 103 | AlQ 300 | LiF - 10 Al - 504 |
| 12 | MPMP 304 | G1 403 | Compound of example 8 104 | AlQ 302 | LiF - 10 Al - 504 |
| 13 | MPMP 302 | G1 404 | Compound of example 7 101 | AlQ 303 | LiF - 10 Al - 505 |
| 14 | MPMP 311 | G1 408 | Compound of example 6 102 | AlQ 304 | LiF - 10 Al - 505 |
| 15 | MPMP 304 | G1 401 | Compound of example 3 103 | AlQ 305 | LiF - 10 Al - 505 |
| 16 | MPMP 303 | G1 403 | Compound of example 5 100 | AlQ 303 | LiF - 10 Al - 502 |

All thicknesses are in Angstroms.

TABLE 2

Device Properties

| Example | Peak Radiance cd/m$^2$ | Peak Efficiency cd/A |
|---|---|---|
| Comparative A | 8500 at 18 V | 22 at 15 V |
| 9 | 11000 at 17 V | 24 at 14 V |
| 10 | 12000 at 19 V | 23 at 14 V |
| 11 | 11000 at 17 V | 25 at 13 V |
| 12 | 9000 at 17 V | 24 at 13 V |
| 13 | 9000 at 17 V | 23 at 23 V |
| 14 | 9200 at 17 V | 30 at 13 V |
| 15 | 11000 at 17 V | 25 at 12 V |
| 16 | 9000 at 18 V | 17 at 15 V |

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Many aspects and embodiments have been described above and are merely exemplary and not limiting. After reading this specification, skilled artisans appreciate that other aspects and embodiments are possible without departing from the scope of the invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed:

1. A compound of the formula:

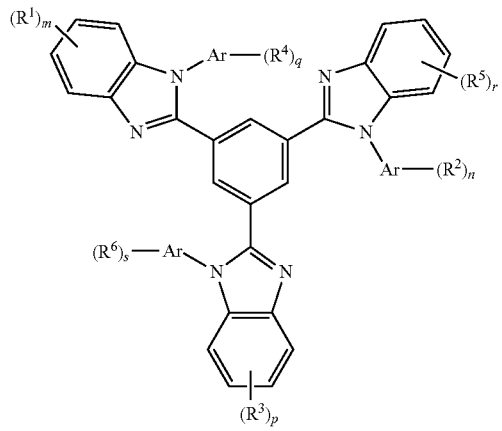

wherein:
- $R^1$, $R^3$, and $R^5$ are each independently H, $C_1$-$C_{20}$ alkyl, halo, $C_1$-$C_{20}$ fluoroalkyl, $C_6$-$C_{20}$ aryl, $C_4$-$C_{20}$ heteroaryl, $C_1$-$C_{20}$ alkoxy, $C_6$-$C_{20}$ aryloxy, $C_1$-$C_{20}$ thioalkoxy, $C_6$-$C_{20}$ thioaryloxy, amino, carboxyl, cyano, nitro, or two adjacent R groups together can be —O—$(CH_2)_t$—O—;
- $R^2$, $R^4$ and $R^6$ are each independently H, halo, $C_1$-$C_6$ alkyl, $C_1$-$C_{20}$ fluoroalkyl, $C_6$-$C_{20}$ aryl, $C_4$-$C_{20}$ heteroaryl, or two adjacent R groups together can be —O—$(CH_2)_t$—O—;
- Ar is phenyl;
- m, n, p, q, r, and s are each independently 0 or an integer from 1 to 3; and
- t is an integer from 1-6;
- provided that (i) at least one of m, r, and p are other than 0 and at least one of $R^1$, $R^3$, and $R^5$ is halo, $C_1$-$C_{20}$ fluoroalkyl, or two adjacent R groups together can be —O—$(CH_2)_t$—O— or (ii) at least one of n, q, and is other than 0 and at least one of $R^2$, $R^4$ and $R^6$ is halo, $C_1$-$C_{20}$ fluoroalkyl, or two adjacent R groups together can be —O—$(CH_2)_t$—O.

2. The compound of claim 1, wherein $R^1$, $R^2$, and $R^3$ are H.

3. The compound of claim 1 wherein $R^2$, $R^4$ and $R^6$ are each independently H, $C_1$-$C_6$ alkyl, F, $CF_3$ or phenyl.

4. The compound of claim 1 wherein m, n, p, q, r, and s are each independently 0 or 1.

5. The compound of claim 1 wherein $R^1$-$R^6$ are each, independently, H, F, $CF_3$, or phenyl, and m, n, p, q, r, and s are each independently 0 or 1.

6. The compound of claim 1 wherein the compound is of the formula:

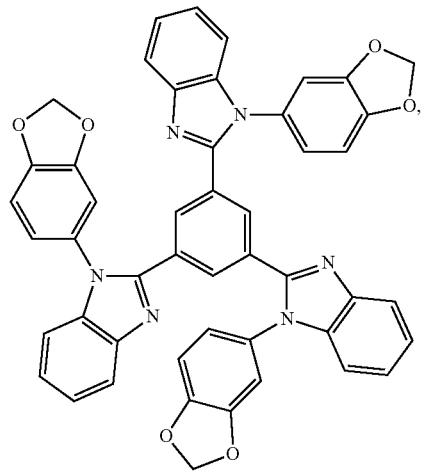

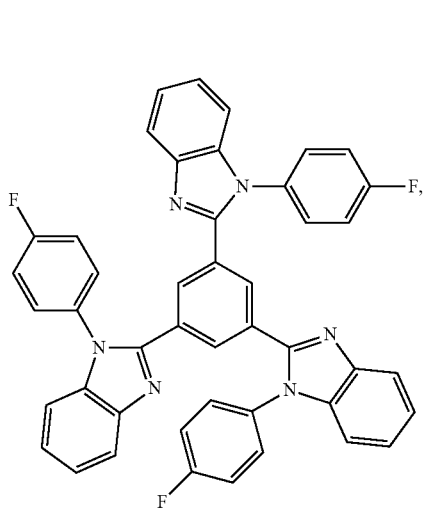

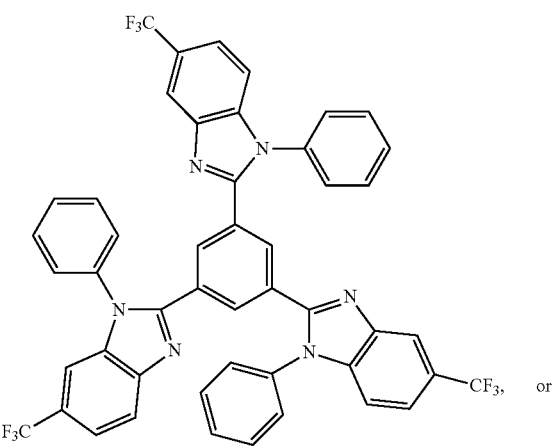

or

-continued

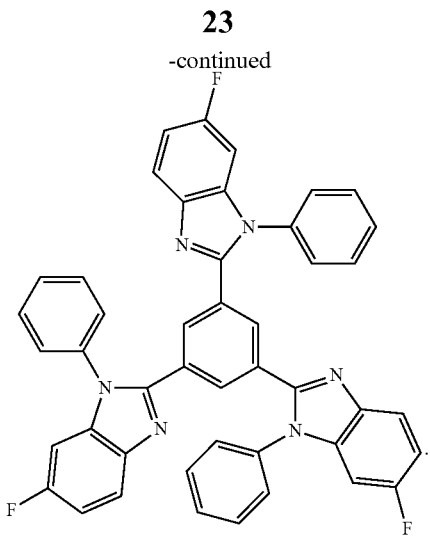

7. The compound of claim 1 having a Tg greater than 125° C.

8. The compound of claim 1 having charge transport properties.

9. The compound of claim 8 having electron transport properties.

10. A composition comprising a compound of claim 1, and a solvent, a processing aid, a charge transporting material, a charge blocking material, or combinations thereof.

11. An electronic device comprising a charge transport layer comprising a compound of claim 1.

12. The electronic device of claim 11, wherein the device is an organic light-emitting diode, a diode laser, a photodetector, a photoconductive cell, a photoresistor, a photo switch, a phototransistor, a phototube, an IR detector, a photovoltaic cell, a solar cell, a light sensor, a thin film organic transistor, a photoconductor, or an electrophotographic device.

13. The electronic device of claim 11, wherein the device is an organic light-emitting device.

14. The electronic device of claim 11 comprising at least one layer comprising at least one compound of the formula:

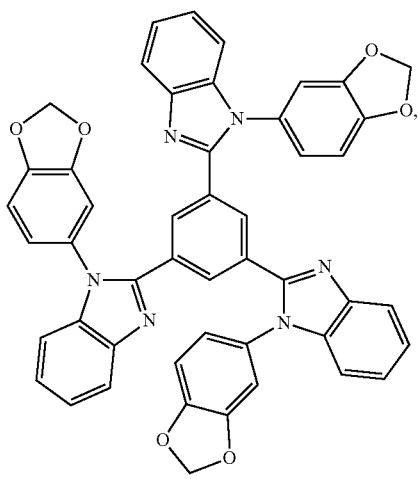

-continued

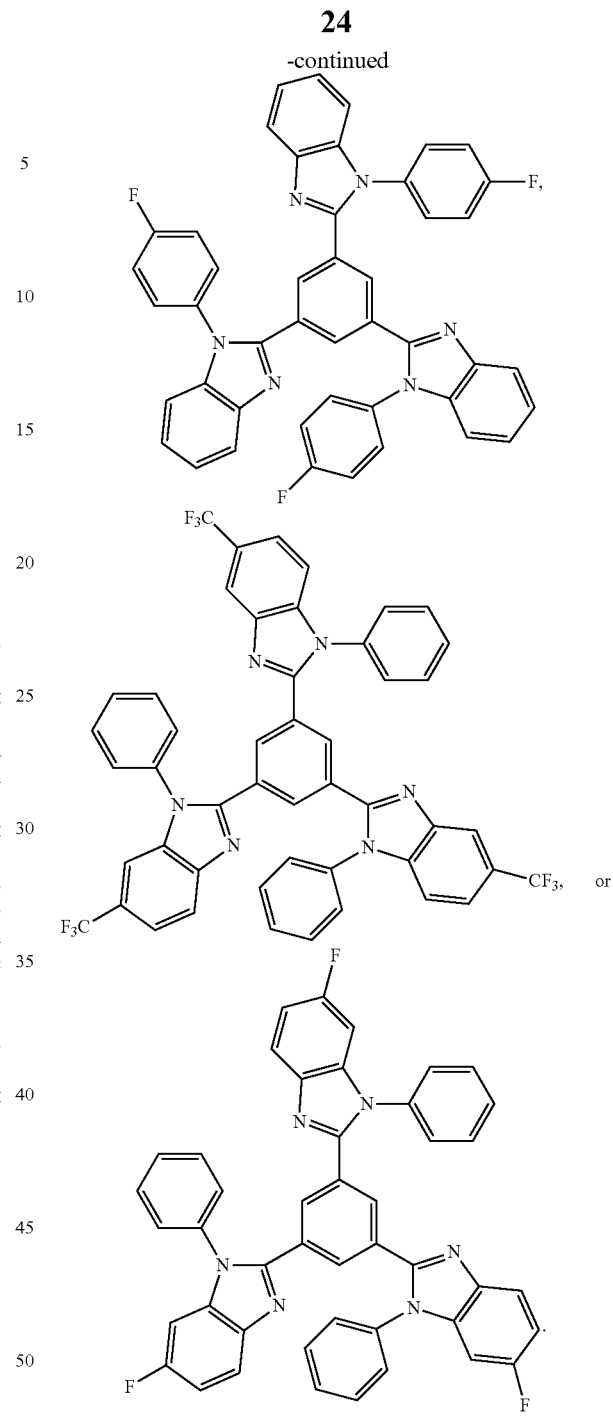

15. An article useful in the manufacture of an organic electronic device comprising the compound of claim 1.

16. A charge transport layer comprising a compound of claim 1.

17. The compound of claim 1 wherein Ar is phenyl; r, p and m are 0; $R^2$, $R^4$, and $R^6$ are F; and q, n, and s are 1.

* * * * *